US009433967B2

(12) United States Patent
Asano

(10) Patent No.: US 9,433,967 B2
(45) Date of Patent: Sep. 6, 2016

(54) PATTERN INSPECTION METHOD, PATTERN FORMATION CONTROL METHOD, AND PATTERN INSPECTION APPARATUS

(71) Applicant: KABUSHIKI KAISHA TOSHIBA, Minato-ku, Tokyo (JP)

(72) Inventor: Masafumi Asano, Yokohama (JP)

(73) Assignee: Kabushiki Kaisha Toshiba, Tokyo (JP)

(*) Notice: Subject to any disclaimer, the term of this patent is extended or adjusted under 35 U.S.C. 154(b) by 25 days.

(21) Appl. No.: 14/283,339

(22) Filed: May 21, 2014

(65) Prior Publication Data
US 2015/0235911 A1     Aug. 20, 2015

(30) Foreign Application Priority Data

Feb. 20, 2014  (JP) ................................ 2014-030384

(51) Int. Cl.
| | |
|---|---|
| *B05C 9/14* | (2006.01) |
| *B05C 21/00* | (2006.01) |
| *G03F 7/00* | (2006.01) |
| *G02F 1/01* | (2006.01) |
| *C09K 11/06* | (2006.01) |
| *G01N 21/64* | (2006.01) |
| *G01N 21/956* | (2006.01) |
| *H01L 21/66* | (2006.01) |

(52) U.S. Cl.
CPC ............ *B05C 21/005* (2013.01); *C09K 11/06* (2013.01); *G01N 21/6458* (2013.01); *G01N 21/956* (2013.01); *G02F 1/01* (2013.01); *G03F 7/0002* (2013.01); *H01L 22/12* (2013.01)

(58) Field of Classification Search
None
See application file for complete search history.

(56) References Cited

U.S. PATENT DOCUMENTS

| | | | |
|---|---|---|---|
| 7,829,546 B2 | 11/2010 | Kawai et al. | |
| 2003/0162215 A1 | 8/2003 | Iwao et al. | |
| 2008/0050659 A1 | 2/2008 | Ohtake et al. | |
| 2012/0234465 A1* | 9/2012 | Wen ................. | C08L 71/02 156/99 |
| 2014/0154630 A1* | 6/2014 | Schmid ............. | G03F 7/0002 430/323 |

FOREIGN PATENT DOCUMENTS

| | | |
|---|---|---|
| JP | 2003-322654 | 11/2003 |
| JP | 2010-151848 | 7/2010 |
| WO | WO 2006/035659 | 4/2006 |

OTHER PUBLICATIONS

Kihara, N., "Directed Self-Assembly Lithography Technology," Special Reports, Toshiba Review, vol. 67, No. 4, pp. 44-47, (2012).
Aoki, H. et al., "Quantitative Analysis of End-to-End Distance of Single Polymer Chain in Ultra-Thin Film by Super-Resolution Fluorescence Imaging," Chemical Physics, No. 419, pp. 54-56, (2013).

* cited by examiner

*Primary Examiner* — Charles Garber
*Assistant Examiner* — Stanetta Isaac
(74) *Attorney, Agent, or Firm* — Finnegan, Henderson, Farabow, Garrett & Dunner LLP

(57) ABSTRACT

According to one embodiment, in a pattern inspection method, a guide pattern is formed on a substrate. A block copolymer is applied on the guide pattern. Thereafter, the substrate is heated according to a predetermined heating condition to promote directed self assembly corresponding to a shape of the guide pattern with respect to the block copolymer. Further, the substrate is observed by a fluorescence microscope during heating or after heating the substrate.

8 Claims, 11 Drawing Sheets

FIG.5
(a) 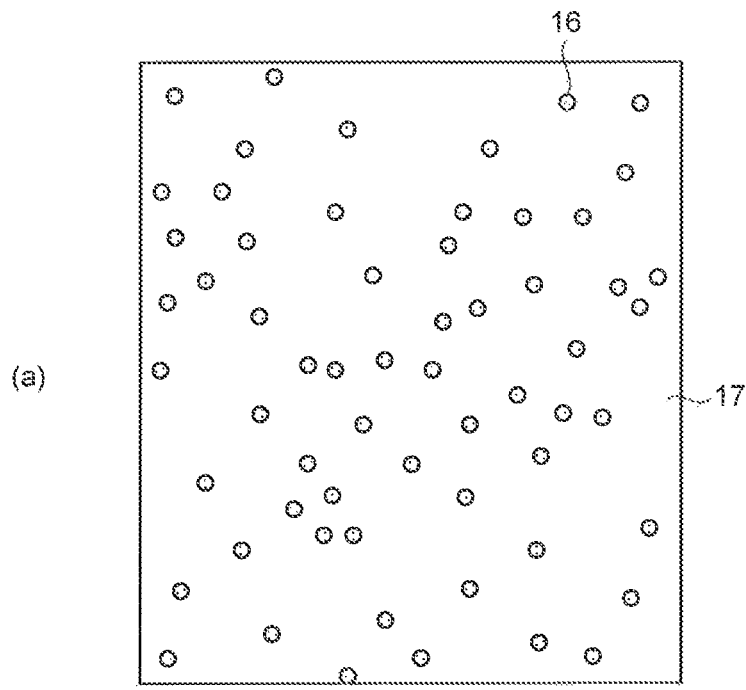
(b) 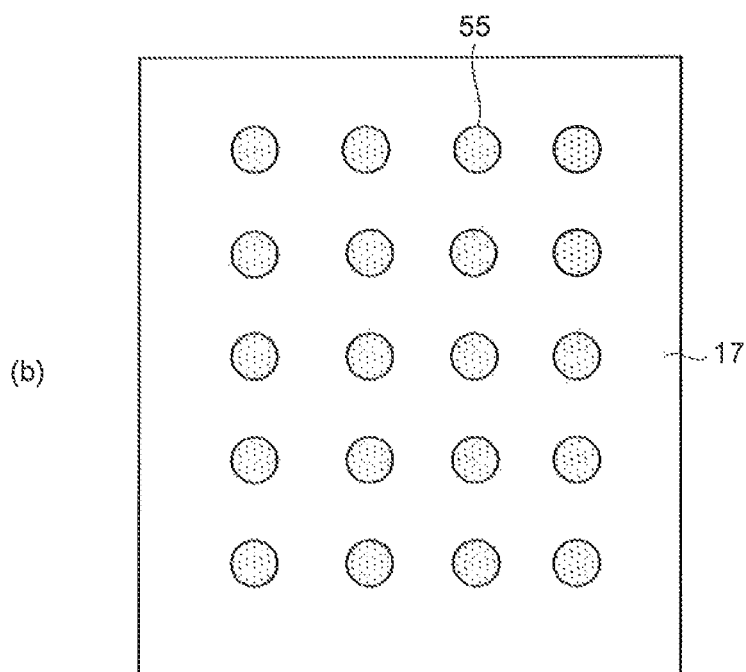

FIG.7
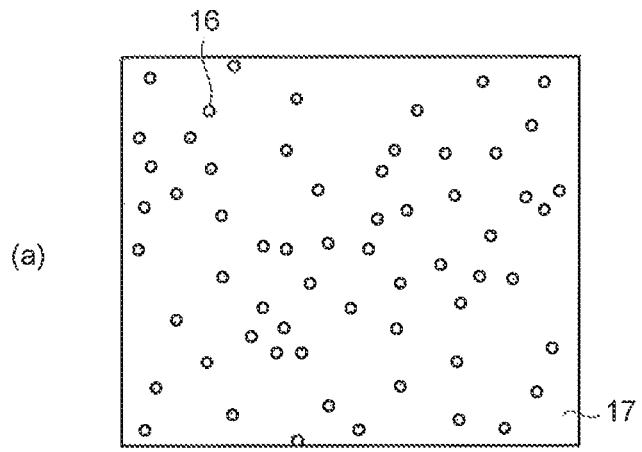
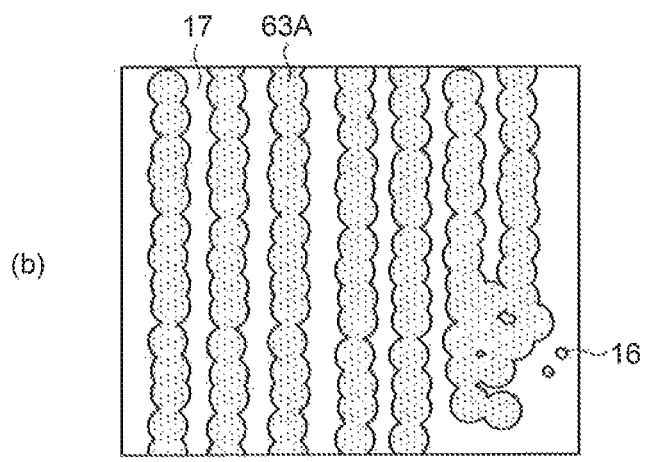
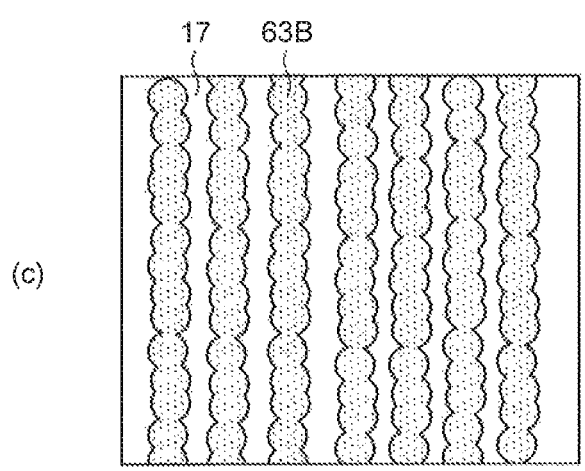

PATTERN INSPECTION METHOD, PATTERN FORMATION CONTROL METHOD, AND PATTERN INSPECTION APPARATUS

CROSS-REFERENCE TO RELATED APPLICATIONS

This application is based upon and claims the benefit of priority from Japanese Patent Application No. 2014-030384, filed on Feb. 20, 2014; the entire contents of which are incorporated herein by reference.

FIELD

Embodiments described herein relate generally to a pattern inspection method, a pattern formation control method, and a pattern inspection apparatus.

BACKGROUND

As a technique for next-generation lithography process, in recent years, a DSA (Directed Self Assembly) process is gaining attention. To apply the DSA process in a manufacturing process of a semiconductor device, it is necessary to uniformly promote a microphase separation reaction in a substrate to be processed. In the microphase separation reaction, there is required high controllability such as (1) composition of material, (2) shape of guide pattern, and (3) heating process.

However, it has been difficult to inspect as to what type of pattern is formed by DSA. Therefore, development of a technique for easily inspecting a pattern formed by DSA has been desired.

BRIEF DESCRIPTION OF THE DRAWINGS

FIGS. 5A and 5B are explanatory diagrams of phase separation of a block copolymer at the time of forming a fine hole pattern on a wafer;

FIGS. 7A to 7C are explanatory diagrams of phase separation of a block copolymer at the time of forming a fine line and space pattern on a wafer;

DETAILED DESCRIPTION

In general, according to one embodiment, a pattern inspection method includes a guide pattern forming step, an applying step, a heating step, and an observing step. At the guide pattern forming step, a guide pattern is formed on a substrate. At the applying step, a block copolymer is applied on the guide pattern. At the heating step, the substrate is heated according to a predetermined heating condition to promote directed self assembly corresponding to a shape of the guide pattern with respect to the block copolymer. Further, at the observing step, the substrate is observed by a fluorescence microscope during heating or after heating the substrate.

Exemplary embodiments of a pattern inspection method, a pattern formation control method, and a pattern inspection apparatus will be explained below in detail with reference to the accompanying drawings. The present invention is not limited to the following embodiments.

(First Embodiment)

Figure 1:
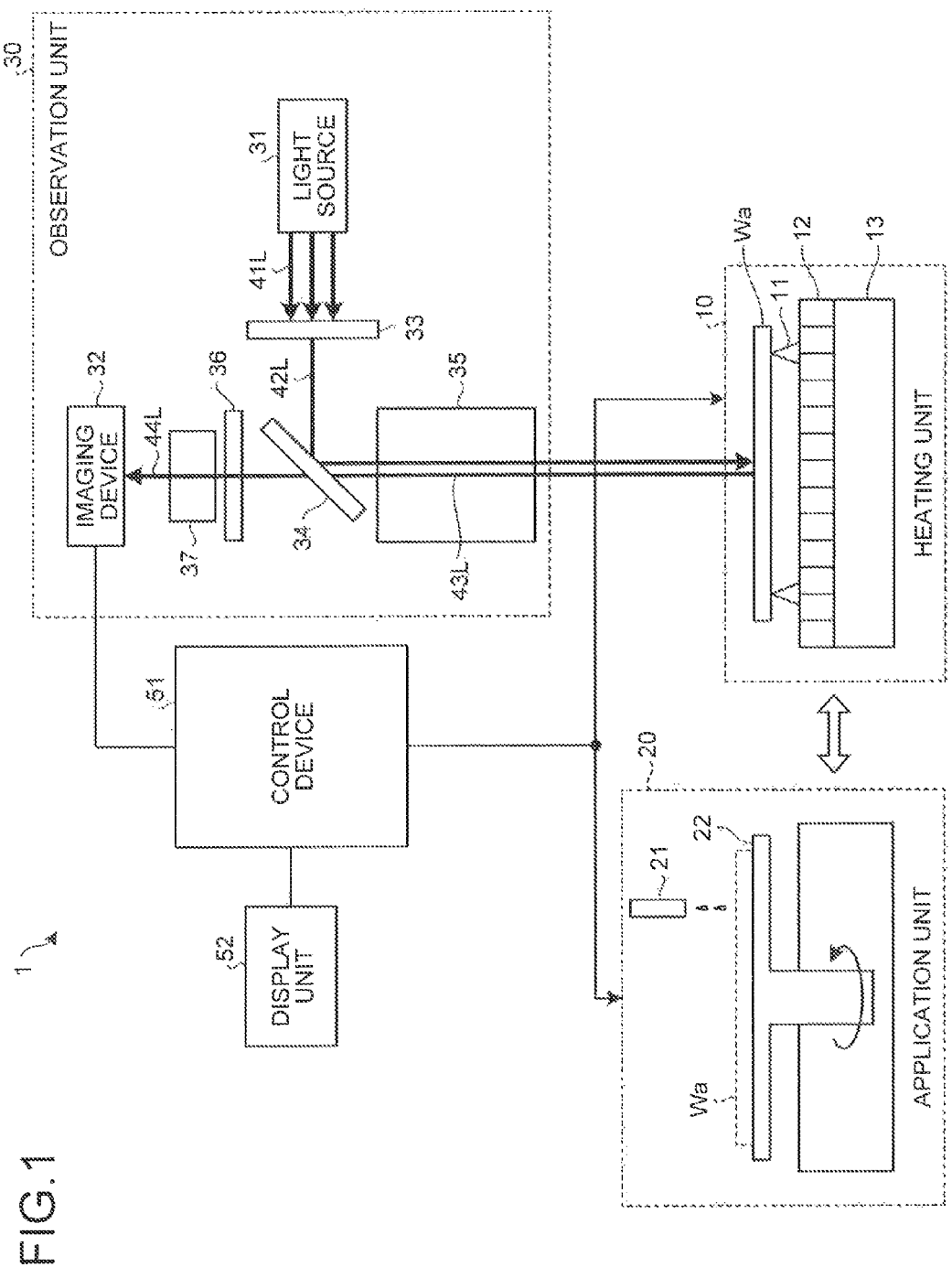
FIG. 1 illustrates a configuration of a pattern inspection apparatus according to an embodiment.

FIG. 1 illustrates a configuration of a pattern inspection apparatus according to a first embodiment. A pattern inspection apparatus 1 is an apparatus that inspects a formation status of a DSA pattern at the time of performing a DSA (Directed Self Assembly) process by using a fluorescence labeling method. The pattern inspection apparatus 1 includes a heating unit 10, an application unit 20, an observation unit 30, a control device 51, and a display unit 52.

The heating unit 10 heats a substrate to be processed (for example, a wafer Wa) in the DSA process. The DSA process is a process in which after a guide pattern (an induction pattern) is formed, a DSA material is self-assembled (phase-separated) on the guide pattern or between guide patterns (guide areas), thereby forming the DSA pattern (a pattern after phase separation). The directed self assembly is performed by heating the DSA material arranged on the guide pattern or between the guide patterns. By heating the wafer Wa on which the DSA material is applied, the heating unit 10 self-assembles the DSA material.

In the first embodiment, a block copolymer is used as the DSA material. The block copolymer has polymethyl methacrylate (PMMA) and polystyrene (PS), for example. Further, in the block copolymer, a part of the PMMA may be replaced by perylene.

The heating unit 10 includes a supporting unit 11, a hot plate 12, and a heating control unit 13. The supporting unit 11 is configured by a pin-like member and supports the wafer Wa from a bottom surface thereof. The supporting unit 11 is arranged on a top surface of the hot plate 12.

The hot plate 12 heats the wafer Wa from the bottom surface thereof. On the hot plate 12, a heating area is divided into a plurality of blocks, and is configured so as to control the heating temperature in each of the blocks. With this configuration, the hot plate 12 performs a temperature adjustment in each position within a wafer surface. For example, the hot plate 12 increases the tempera lure of a block in a position that is later than the other positions in the progress of directed self assembly to be higher than a reference temperature. In addition, for example, the hot plate 12 reduces the temperature of a block in a position that is advanced more than the other positions in the progress of directed self assembly to be lower than a reference temperature. The heating control unit 13 controls the hot plate 12 according to an instruction from the control device 51.

The application unit 20 applies a DSA material on the wafer Wa. The application unit 20 includes a DSA-material supply unit 21 and a wafer supporting unit 22. The DSA-material supply unit 21 discharges the DSA material on the wafer Wa. The wafer supporting unit 22 places the wafer Wa. By rotating the placed wafer Wa, the wafer supporting unit 22 uniformly widens the DSA material on the wafer Wa, and discharges a redundant part of the DSA material to outside of the wafer Wa.

The observation unit 30 observes the progress status of the DSA process by observing the DSA material on the wafer Wa. The observation unit 30 according to the first embodiment observes a surface of the wafer Wa during heating or after heating the wafer Wa by the heating unit 10. The observation unit 30 is a fluorescence microscope or a scanning laser microscope, for example.

The observation unit 30 includes a light source 31, an imaging device 32, filters 33 and 36, a dichroic mirror 34, an objective lens 35, and a relay lens 37. The light source 31 outputs excitation beams 41L and sends the beams to the filter 33. The filter 33 selectively transmits only a predetermined excitation beam 42L among the excitation beams 41L.

The dichroic mirror 34 is a mirror that reflects an excitation beam and transmits fluorescence. In this example, the dichroic mirror 34 reflects the excitation beam 42L to induce it to the objective lens 35. The dichroic mirror 34 then transmits fluorescence 43L sent from the objective lens 35 to the imaging device 32.

The objective lens 35 collects the excitation beam 42L to irradiate it on the wafer Wa. When the excitation beam 42L is reflected on the wafer Wa, the fluorescence 43L as a reflected beam is sent to the objective lens 35. The fluorescence 43L is sent to the filter 36 via the objective lens 35 and the dichroic mirror 34.

The filter 36 selectively transmits only predetermined, fluorescence 44L among the fluorescence 43L to send the fluorescence 44L to the relay lens 37. The relay lens 37 sends the fluorescence 44L to the imaging device 32. The imaging device 32 generates a surface image of the wafer Wa based on the fluorescence 44L and sends the generated image to the control device 51.

The control device 31 controls the heating unit 10, the application unit 20, the observation unit 30, and the display unit 52. The control device 51 causes the display unit 52 to display the surface image of the wafer Wa. The display unit 52 displays the surface image of the wafer Wa in real time.

The DSA material is applied on the wafer Wa by the application unit 20, and then transferred to the heating unit 10 by a transfer unit (not shown). Subsequently, the wafer Wa is heated by the heating unit 10. With this process, the directed self assembly of the DSA material is promoted on the wafer Wa. At this time, the observation unit 30 observes the progress status of the DSA process in real time. The display unit 52 then displays the progress status (a surface image of the wafer Wa) of the DSA process.

Figure 2:
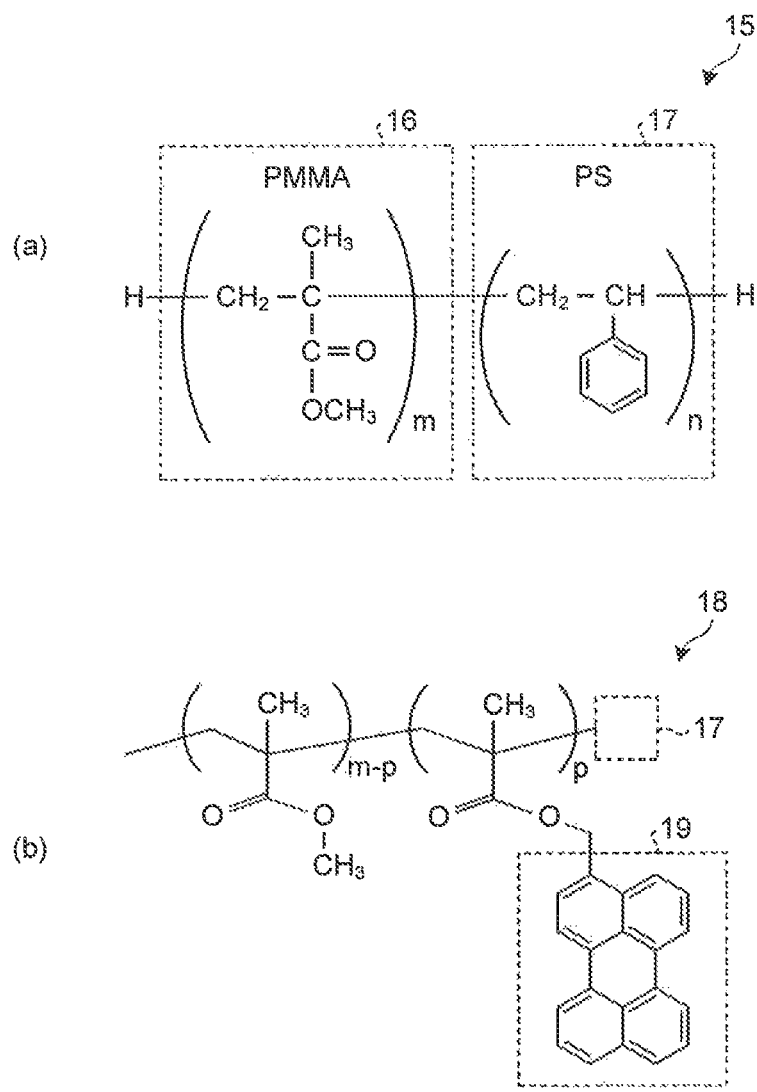
FIGS. 2A and 2B illustrate a configuration of a DSA material.

The DSA material is explained here. FIGS. 2A and 2B illustrate a configuration of a DSA material. A first DSA material shown in FIG. 2A is a block copolymer 15. The block copolymer 15 has m (m is a natural number) PMMAs 16 and n (n is a natural number) PSs 17.

Further, a second DSA material shown in FIG. 2B is a block copolymer 18. The block copolymer 18 is a block copolymer such that methyl groups in side chains of a part of PMMAs 16 among the PMMAs 16 included in the block copolymer 15 are replaced by perylene 19 as fluorescent molecules. For example, the block copolymer 18 is a block copolymer such that methyl groups in side chains of p (p is a natural number less than m) PMMAs 16 among m PMMAs 16 included in the block copolymer 15 are replaced by the perylene 19.

The volume ratio of the PMMA 16 with respect to the block copolymer 15 or 18 is approximately 30%, for example. In the following explanations, there is described a case where an inspection of a DSA pattern is performed with reference to the block copolymer 18 in which a part of the PMMAs 16 is replaced by the perylene 19.

Figure 3:
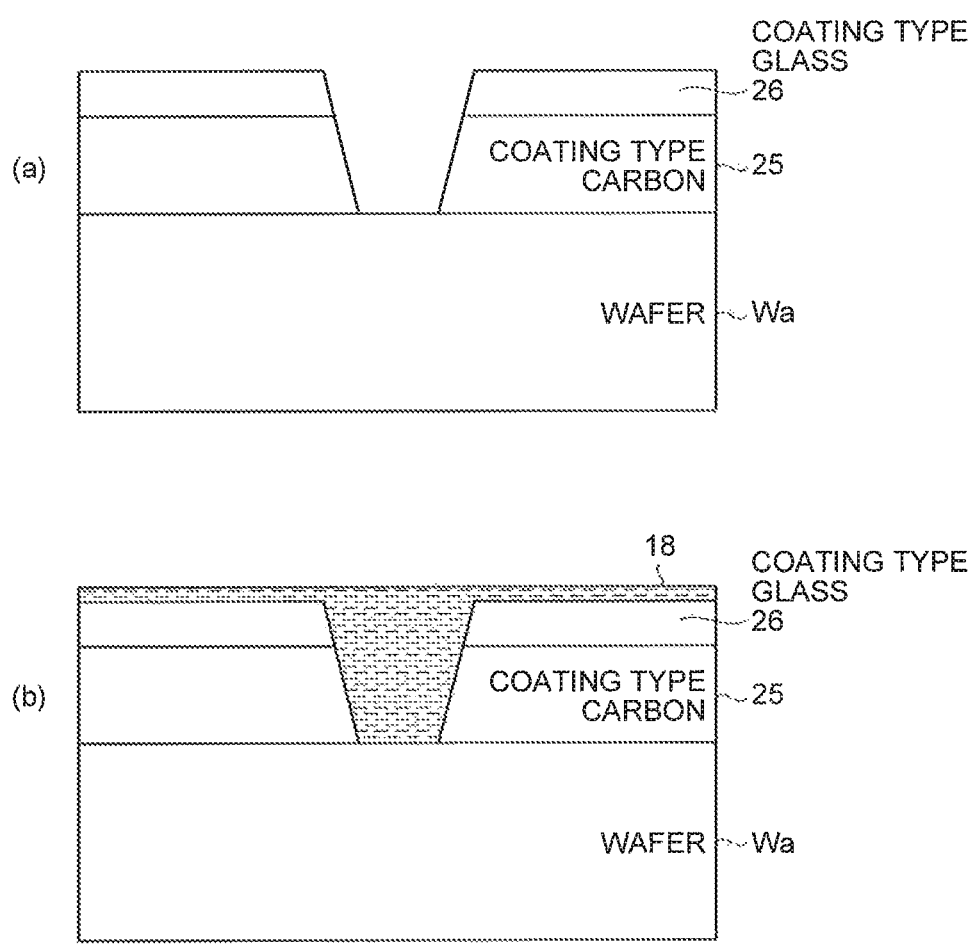
FIGS. 3A and 3B are explanatory diagrams of an application process of a block copolymer.

FIGS. 3A and 3B are explanatory diagrams of an application process of a block copolymer. In the DSA process, a carbon film such as coating type carbon 25 and coating type glass 26 are coated in this order on the wafer Wa (such as a silicon substrate). Thereafter, by lithography and etching, a hole pattern (a guide pattern) having a diameter of approximately 70 nanometers shown in FIG. 3A is formed in the coating type carbon 25 and the coating type glass 26.

Next, as shown in FIG. 3B, the block copolymer 18 having the perylene 19 introduced therein is spin-coated on the wafer Wa in which a hole pattern, (hereinafter, "guide hole pattern") as a guide pattern is formed. Thereafter, the wafer Wa is heated by the heating unit 10. With this process, when heat is added to the block copolymer 18, a microphase separation reaction of the block copolymer 18 is accelerated and the directed self assembly is promoted. For example, the observation unit 30 observes the wafer Wa from the start of the heating. With this process, fluorescence from the perylene 19 is observed.

Figure 4:
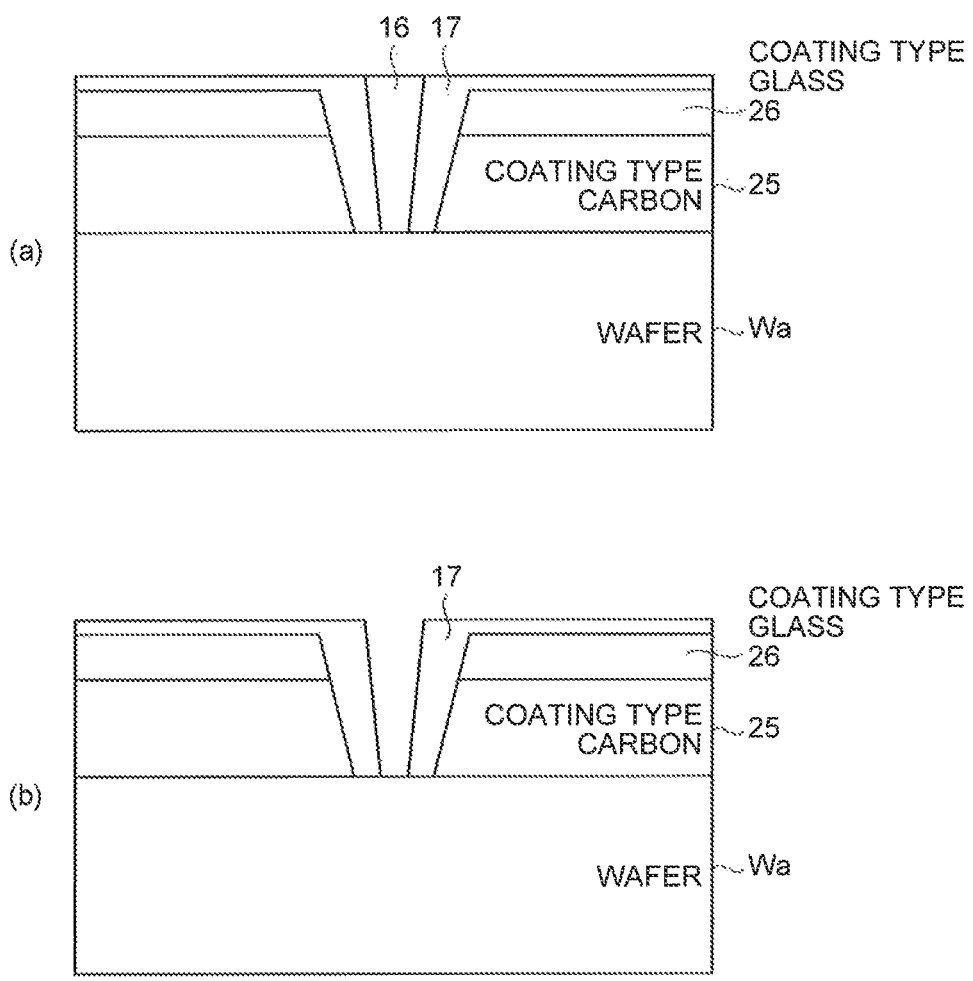
FIGS. 4A and 4B illustrate a fine hole pattern formed in a DSA process.

FIGS. 4A and 4B illustrate a fine hole pattern formed in the DSA process. In FIGS. 4A and 4B, cross-sectional views of the wafer Wa are shown. When the block copolymer 18 is heated, the PMMAs 16 and the PSs 17 assemble in the guide hole pattern as shown in FIG. 4A. In a portion other than the guide hole pattern, phase separation of the block copolymer 18 is not promoted and the block copolymer 18 is left on the wafer Wa as it is.

After finishing the heating, when irradiation of VUV light and alkali development are performed on the wafer Wa, the PMMAs 16 are removed from the wafer Wa as shown in FIG. 4B. With this process, an outer peripheral portion of the guide hole pattern is filled with the PS 17, and a central portion of the guide hole pattern is hollowed out. As a result, it is possible to obtain a hole pattern that is finer than the guide hole pattern formed by the coating type carbon 25 and the coating type glass 26. Thereafter, an actual hole pattern corresponding to the shape and size of the PS 17 is formed on the wafer Wa when the wafer Wa is etched by using the PS 17, the coating type carbon 25, and the coating type glass 26, as a mask.

FIGS. 5A and 5B are explanatory diagrams of phase separation of a block copolymer at the time of forming a fine hole pattern on a wafer. FIGS. 5A and 5B illustrate an upper surface of the wafer Wa on which the block copolymer 18 is applied. The PMMA 16 having the perylene 19 is shown in FIG. 5A, and a set (a PMMA group 55) of the PMMA 16 having the perylene 19 is shown in FIG. 5B. In FIG. 5A, the PS 17 is present in a portion other than the PMMA 16. Further, in FIG. 5B, the PS 17 is present around the PMMA group 55.

As shown in FIG. 5A, distribution of the PMMAs 16 indicating fluorescence is random in a field of view before the start of heating. As the heating proceeds, the distribution of the PMMAs 16 starts to line up in an orderly manner according to the arrangement of a guide hole pattern. The reason for this is that the phase separation of the block copolymer 18 is being promoted. The heating unit 10 continues the heating until a movement in the distribution of the PMMAs 16 stops, that is, the phase separation reaction converges. With this process, on the guide hole pattern, the PMMAs 16 are formed into the PMMA group 55 including a plurality of the PMMAs 16. The shape of the PMMA group 55 corresponds to that of the guide hole pattern.

After finishing the heating, when irradiation of VUV light and alkali development are performed on the wafer Wa, the PMMAs 16 are removed from the wafer Wa. Subsequently, as shown in FIG. 5B, the PMMA group 55 including a plurality of the PMMAs 16 is formed on the guide hole pattern.

As described above, before the start of heating, the block copolymers 18 are randomly entwined with each other in the guide hole pattern. Subsequently, by heating the block copolymer 18, the microphase separation occurs. As a result, molecules move so that the PSs 17 are aligned in a wail portion on the guide hole pattern and the PMMAs 16 are aligned inside the guide hole pattern. Because the perylene 19 is given to the PMMA 16, light is emitted in a position where the PMMA 16 is present. Therefore, when the wafer Wa is observed by the observation unit 30 such as a fluorescence microscope, the position where the PMMA 16 is present, can be observed. Accordingly, a movement of the PMMA 16 can be monitored in real time in a phase separation process.

An observation result of such observation mentioned above can be used for an inspection of the DSA process, or for process control (DSA process control) of the DSA process. In the inspection of the DSA process, for example, a determination of acceptance of a pattern generated by the DSA process is performed. The determination of acceptance is performed by the control device 51.

When the observation result is used for the inspection of the DSA process, the determination of acceptance of the DSA process is performed based on a relationship between the arrangement position and the shape of the PMMA group 55 and between those of the guide contact hole. The imaging device 32 captures a surface image of the wafer Wa and sends the captured image to the control device 51. With this process, based on the surface image of the wafer Wa, the control device 51 derives the arrangement position and the shape of the PMMA group 55. Further, the control device 51 obtains the arrangement position and the shape of the guide contact hole from design data and the like.

Further, it is also possible that the pattern inspection apparatus 1 observes the surface of the wafer Wa to obtain the arrangement position of the guide contact: hole before applying the block copolymer 18 and after forming the coating type carbon 25 and the coating type glass 26. In this case, the imaging device 32 captures the surface image of the wafer Wa and sends the captured image to the control device 51. Subsequently, based on the surface image of the wafer Wa, the control device 51 derives the arrangement position and the shape of the guide contact hole.

Based on the obtained arrangement, position and shape of the PMMA group 55 and the obtained arrangement position and shape of the guide contact hole, the control device 51 determines whether a DSA pattern (a contact hole) with a desired shape is formed in a desired position on the wafer Wa. The determination of acceptance regarding the pattern is performed, for example, in each position of the wafer Wa.

The determination of acceptance regarding the pattern generated by the DSA process can be also performed by a user. Also in this case, the imaging device 32 obtains the arrangement position of the PMMA group 55. Subsequently, the user performs the determination of acceptance regarding the pattern based on the arrangement position of the PMMA group 55 obtained by the imaging device 32 and the arrangement position of the guide contact hole of the design data and the like.

When the observation result is used for the DSA process control, the control device 51 or a user changes a processing condition (such as a heating condition) of the DSA process based on the determination of acceptance regarding the pattern. The determination of acceptance regarding the pattern in this case can be performed by the control device 51 or a user. The control device 51 or the user can change the processing condition of the DSA process in real time, or change the wafer Wa to be processed thereafter.

As the heating condition of the DSA process, for example, the control device 51 changes the heating temperature, the heating time, and a method for increasing or decreasing the heating temperature (a temperature increasing or decreasing process) of the heating unit 10. Further, the control device 51 can change the processing condition in. each position of the wafer Wa. For example, the control device 51 changes a central portion of an area having determined to be unaccepted into a first processing condition and changes the outer peripheral portion of an area having determined to be unaccepted into a second processing condition.

The control device 51 sends positions on the wafer Wa on which the processing condition is changed and change contents of the processing condition set in each of the positions to the heating control unit 13. With this process, the heating control unit 13 controls the hot plate 12 based on. the processing condition changed in each of the positions of the wafer Wa.

The control device 51 can change a heating atmosphere as the processing condition of the DSA process. Further, in the first embodiment, while a case where the heating condition of the wafer Wa is changed as the processing condition of the DSA process, the composition ratio of the block copolymer 18 can be changed.

As described above, the pattern inspection apparatus 1 includes the observation unit 30, and thus it is possible to observe the progress of the phase separation (the directed self assembly). Further, as fluorescence is observed while it is given to the DSA material, the phase separation can be easily observed and controlled. In addition, because a fluorescence microscope is used, a movement of the DSA material (a polymer molecule) can be monitored in real time. Accordingly, the pattern inspection apparatus 1 can control the DSA process in real time according to the observation result. Specifically, by monitoring the DSA process in real time, the pattern inspection apparatus 1 can execute control such as stopping the process in progress or changing the condition.

As described above, according to the first embodiment, a pattern formed by the DSA process can be easily inspected. Further, the DSA process can be easily controlled.

(Second Embodiment)

Next, a second embodiment is described with reference to FIGS. 6 to 11. In the second embodiment, when a fine line and space pattern is formed by the DSA process, pattern inspection and pattern formation control are performed.

Similarly to the first embodiment, in the second embodiment, the pattern inspection apparatus 1 performs pattern inspection by using the block copolymer 18 in which a part of side chains of the PMMAs 16 is replaced by the perylene 19. Note that, in the second embodiment, the block copolymer 18 in which the volume ratio between the PMMA 16 and the PS 17 is approximately 1:1 is used.

Figure 6:
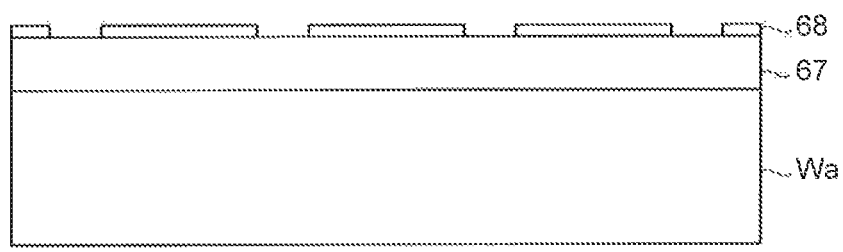
FIG. 6 illustrates a cross-sectional configuration of a wafer used at the time of forming a fine line and space pattern.

FIG. 6 illustrates a cross-sectional configuration of a wafer used at the time of forming a fine line and space pattern. On the wafer Wa, a pattern is formed in advance by a hydrophobic film 67 in which the property of a surface is hydrophobic and a hydrophilic film 68 in which the property of a surface is hydrophilic. The hydrophobic film 67 and the hydrophilic film 68 respectively have a line pattern. For example, the hydrophobic film. 67 and the hydrophilic film 68 are alternately arranged at a 100 nanometer interval. A pattern formed by the hydrophobic film 67 and the hydrophilic film 68 is a guide pattern (hereinafter, "guide L/S pattern").

The pattern inspection apparatus 1 applies the block copolymer 18 on the wafer Wa and performs a heating process. Subsequently, similarly to the first embodiment, the pattern inspection, apparatus 1 observes fluorescence in the heating process.

FIGS. 7A to 7C are explanatory diagrams of phase separation of a block copolymer at the time of forming a fine line and space pattern on a wafer. FIGS. 7A to 7C illustrate an upper surface of the wafer Wa on which the block copolymer 18 is applied. The PMMA 16 having the perylene 19 is shown in FIG. 7A, and a set (PMMA groups 63A and 63B) of the PMMA 16 having the perylene 19 is shown in FIGS. 7B and 7C.

In FIG. 7A, the PS 17 is present in a portion other than the PMMA 16. Further, in FIG. 7B, the PSs 17 are present around the PMMAs 16 and the PMMA group 63A, and in FIG. 7C, the PSs 17 are present around the PMMAs 16 and the PMMA group 63B.

As shown in FIG. 7A, distribution of the PMMA 16 indicating fluorescence is random in a field of view before the start of heating. As the heating proceeds, the distribution of the PMMAs 16 and the PSs 17 starts to line up in an orderly manner according to the arrangement of a guide L/S pattern.

The heating unit 10 continues heating the wafer Wa as long as a predetermined time. With this process, as shown in FIG. 7B, on a hole pattern, the PMMAs 16 are formed into the PMMA group 63A including a plurality of the PMMAs 16. For example, within a predetermined time, a fluorescence pattern (the PMMA group 63A) may be disturbed on a part of the wafer Wa.

In this case, the heating unit 10 extends the heating time. The heating unit 10 continues the heating until a movement of the distribution of the PMMA group 63A and the PMMAs 16 stops, that is, the phase separation reaction converges. Accordingly, a uniform fluorescence pattern is formed on the wafer Wa. Specifically, the PMMA group 63A and the PMMAs 16 are formed into the PMMA group 63B including a plurality of the PMMAs 16 on the guide L/S pattern. The shape of the PMMA group 63B corresponds to that of the guide L/S pattern. In this manner, the shape of the PMMA group 63B corresponds to that of the guide L/S pattern, and thus it becomes possible to recognize that the microphase separation reaction is sufficiently promoted.

After finishing the heating, when irradiation of VUV light and alkali development are performed on the wafer Wa, the PMMAs 16 are removed from the wafer Wa. As a result, it is possible to obtain a line and space pattern that is finer than the guide L/S pattern formed by the hydrophobic film 67 and the hydrophilic film 68. The fine line and space pattern has a pitch of 25 nanometers, for example. Thereafter, an actual hole pattern corresponding to the shape and size of the PS 17 is formed on the wafer Wa when the wafer Wa is etched by using the PS 17 as a mask.

Figure 8:
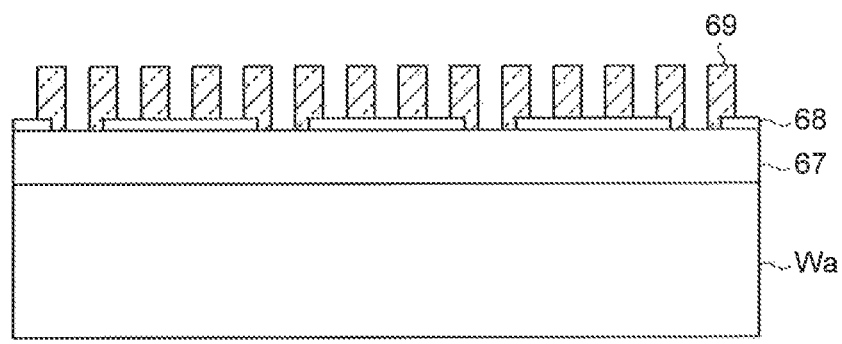
FIG. 8 illustrates a fine line and space pattern formed by the DSA process.

FIG. 8 illustrates a fine line and space pattern formed by the DSA process. In FIG. 8, a cross-sectional view of the wafer Wa is shown. On the wafer Wa, the PMMA group 63B is removed to leave the PS 17. With this process, a line pattern 69 formed by a set of the PS 17 is formed on the wafer Wa.

At this time, the pattern inspection apparatus 1 inspects a pattern formed by the DSA with the same method as that of the first embodiment. Further, the pattern inspection apparatus 1 controls the DSA process with the same method as that of the first embodiment.

The observation unit 30 can be configured by any microscope. For example, the observation unit 30 can be a confocal laser microscope, a STED (Stimulated Emission Depletion) microscope, or a SIM (Structured Illumination Microscopy. Further, the observation unit 30 can be a STORM (Stochastic Optical Reconstruction Microscopy) or a PALM (Photo Activated Localization Microscopy).

Figure 9:
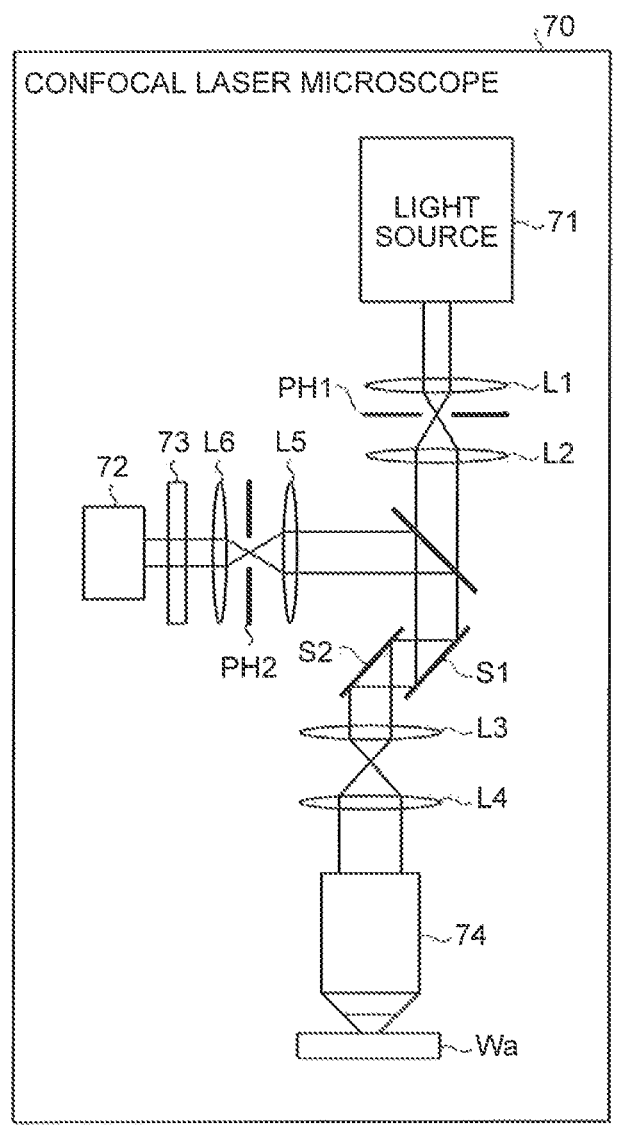
FIG. 9 illustrates a configuration of a confocal laser microscope.

FIG. 9 illustrates a configuration of a confocal laser microscope. A confocal laser microscope 70 includes a light source 71, lenses L1 to L6, pinholes PH1 and PH2, scanners S1 and S2, an objective lens 74, a filter 73, and a detector 72.

In the confocal laser microscope 70, laser light output from the light source 71 is sent to the scanners S1 and S2 via the lens L1, the pinhole PH1, and the lens L2. The laser light is sent from the scanners S1 and S2 to the objective lens 74 via the lenses L3 and L4. Further, the laser light is irradiated on the wafer Wa via the objective lens 74.

Subsequently, the laser light reflected by the wafer Wa is sent to the lens L5 via the objective lens 74, the lenses L4 and L3, and the scanners S2 and S1. Further, the laser light is sent to the detector 72 via the lens L5, the pinhole PH2, the lens L6, and the filter 73. With this configuration, the state of the wafer Wa is detected by the detector 72. In the confocal laser microscope 70 described above, because a redundant part of the laser light is cut by the pinholes PH1 and PH2, the detector 72 can obtain a clear image.

Figure 10:
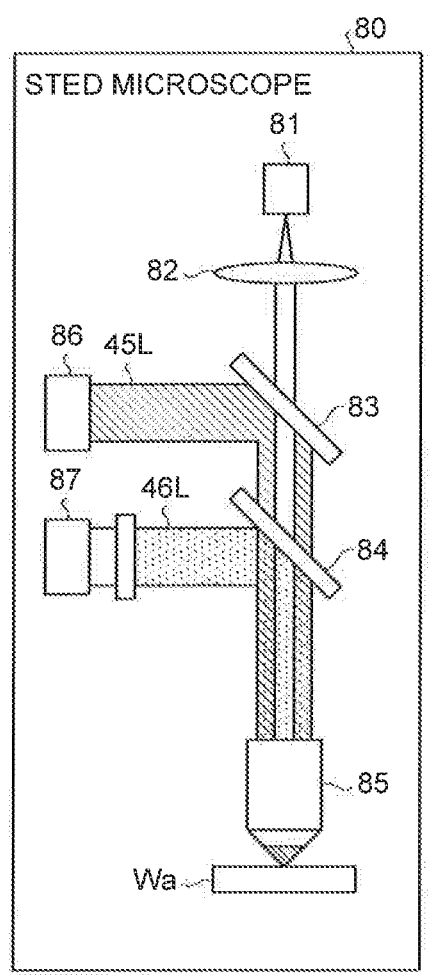
FIG. 10 illustrates a configuration of a STED microscope.
Figure 11:
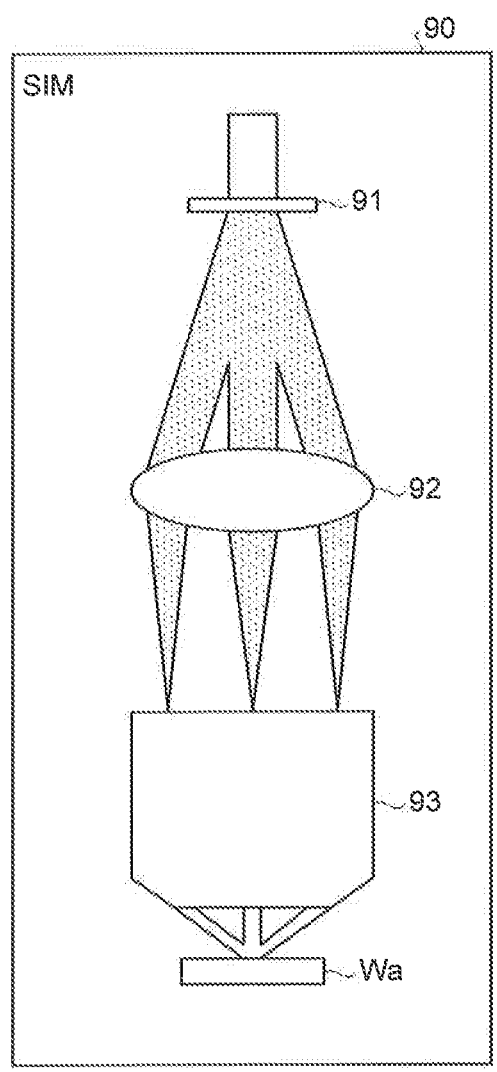
FIG. 11 illustrates a configuration of a SIM.

FIG. 10 illustrates a configuration of a STED microscope. A STED microscope 80 includes light sources 86 and 87, a detector 81, lenses 82 and 85, and dichroic mirrors 83 and 84.

An excitation beam 45L is output from the light source 86, and a STED beam 46L is output from the light source 87. At this time, the intensity in the center of the STED beam 46L is completely equal to 0, and the STED beam 46L is formed in a doughnut shape. The excitation beam 45L is sent to the lens 85 via the dichroic mirrors 83 and 84. Further, the STED beam 46L is sent to the lens 85 via the dichroic mirror 84. Subsequently, these two beams are irradiated on the wafer Wa via the lens 85 substantially at the same time.

Next, the two beams reflected by the wafer Wa are sent to the detector 81 via one lens 85, the dichroic mirrors 84 and 83, and the lens 82. With this process, the state of the wafer Wa is detected by the detector 81.

In the STED microscope 80, the excitation beam 45L and the STED beam 46L are irradiated on the wafer Wa, and as a result, fluorescence in a portion in which the two beams are overlapped with each other is extinguished. As a result, the width of the fluorescence is narrowed.

FIG. 1 illustrates a configuration of a SIM. A SIM 90 includes a grating 91, a lens 92, and an objective lens 93. Note that a light source and a detector of the SIM 90 are not shown in FIG. 11.

In the SIM 90, an excitation beam is irradiated on the wafer Wa via the grating 91, the lens 92, and the objective lens 93. With this process, the SIM 90 analyzes a moire image formed from grating illumination and a surface state of the wafer Wa, and estimates the structure of the wafer Wa.

Pattern inspection and pattern formation control of the wafer Wa are performed for each layer of the wafer process. Subsequently, a semiconductor device (a semiconductor integrated, circuit) is manufactured by using the wafer process. Specifically, after a guide pattern is formed on the wafer Wa, the pattern inspection apparatus 1 applies a DSA material on the guide pattern. While performing the pattern inspection and the pattern formation control, the pattern inspection apparatus 1 performs a heating process on the wafer Wa, thereby self-assembling the DSA material. Thereafter, development of the wafer Wa and the like is performed, thereby forming the DSA pattern on the wafer Wa.

Subsequently, a layer lower than the DSA pattern is etched by using the DSA pattern as a mask. Accordingly, an actual pattern corresponding to the DSA pattern is formed on the wafer Wa. When a semiconductor device is manufactured, the pattern inspection described above, pattern formation control, a development process, an etching process and the like are repeated for each layer.

As described above, according to the second embodiment, a pattern formed by the DSA process can be easily inspected. Further, the DSA process can be easily controlled.

As described above, according to the first and second embodiments, a pattern formed by the DSA process can be easily inspected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pattern inspection apparatus comprising:
    an application unit that applies a block copolymer on a substrate;
    a heating unit that heats the substrate according to a predetermined heating condition, and that promotes directed self assembly of the block copolymer, the directed self assembly corresponding to a shape of a guide pattern formed on the substrate
    an observation unit that observes the substrate by a fluorescence microscope during heating or after heating the substrate; and
    a control unit that changes the heating condition,
    wherein,
    in the heating unit, a heating area of the substrate is divided into a plurality of regions, and
    the control unit changes the heating condition in units of the regions.

2. The pattern inspection apparatus according to claim 1, wherein the control unit performs a determination of acceptance of a pattern that has been generated by the directed self assembly.

3. The pattern inspection apparatus according to claim 2, wherein
    the control unit performs the determination of acceptance based on an arrangement position of the pattern and an arrangement position of the guide pattern.

4. The pattern inspection apparatus according to claim 1, wherein the control unit changes a heating temperature, which is the heating condition, of the substrate.

5. The pattern inspection apparatus according to claim 1, wherein the control unit changes a heating time, which is the heating condition, of the substrate.

6. The pattern inspection apparatus according to claim 1, wherein the control unit changes a temperature increasing or decreasing process, which is the heating condition, of the substrate.

7. The pattern inspection apparatus according to claim 1, wherein the control unit changes a heating atmosphere, which is the heating condition, of the substrate.

8. The pattern inspection apparatus according to claim 1, further comprising a display device that displays an image of the substrate observed by the fluorescence microscope.

* * * * *